United States Patent [19]

Denise et al.

[11] Patent Number: 4,500,646

[45] Date of Patent: Feb. 19, 1985

[54] CONVERSION CATALYSTS FOR SYNTHESIS GAS

[75] Inventors: Bernard Denise, Rillieux; Christian Hamon, Saint Nazaire; Michel Sénès, La Baule; Raymond Sneeden, Villefontaine, all of France

[73] Assignee: Societe Chimique de la Grande Paroisse, Azote et Producits Chimiques, Paris, France

[21] Appl. No.: 457,411

[22] Filed: Jan. 12, 1983

[30] Foreign Application Priority Data

Jan. 14, 1982 [FR] France .................. 82 00498
Jun. 25, 1982 [FR] France .................. 82 11134

[51] Int. Cl.³ .................. B01J 29/18; B01J 29/24
[52] U.S. Cl. .................. 502/78; 518/713; 518/714
[58] Field of Search .................. 502/78; 252/455 Z; 518/713, 714

[56] References Cited

U.S. PATENT DOCUMENTS

| 3,551,353 | 12/1970 | Chen et al. | 252/455 |
|---|---|---|---|
| 3,673,267 | 6/1972 | Chen et al. | 502/78 |
| 4,011,275 | 3/1977 | Zahnet | 518/714 |
| 4,131,568 | 12/1978 | Bartish | 252/455.2 |
| 4,180,516 | 12/1979 | Chang et al. | 502/78 |
| 4,410,637 | 10/1983 | Kortbeek et al. | 518/713 |

FOREIGN PATENT DOCUMENTS

| 1222620 | 4/1982 | Canada . |
|---|---|---|
| 0018683 | 4/1980 | European Pat. Off. . |
| 2019913 | 10/1969 | France . |
| 2320923 | 3/1977 | France . |
| 7803707 | 1/1974 | Netherlands . |

OTHER PUBLICATIONS

Jong et al., Chim. Org., Univ. Poitiers, 86022, C. R. Hebd. Seances Acad. Sci., Ser. C, 1979, 288, (Fr.), "The Conversion of Meorl to Hydrocarbon".

Primary Examiner—Delbert E. Gantz
Assistant Examiner—Chung K. Pak
Attorney, Agent, or Firm—Browdy and Neimark

[57] ABSTRACT

Conversion of the synthetic gas mixtures: carbon monoxide - hydrogen or carbondioxide - hydrogen is carried out in the presence of a catalyst constituted by the association of at least two transition metal elements with an acitve mordenite selected from among de-aluminized acid mordenites. The metal elements can be copper, zinc and chromium. The transition metal elements - active mordenite association can be employed in separate catalytic beds, the first bed being metallic in nature and the second zeolitic in nature. The process is applicable to the manufacture of organic products such as saturated and unsaturated hydrocarbons, particularly light olefines.

7 Claims, No Drawings

CONVERSION CATALYSTS FOR SYNTHESIS GAS

FIELD OF THE INVENTION

The present invention made with the co-operation of the CNRS (Catalysis Research Institute) relates to the catalytic conversion of synthesis gas for the production of organic compounds. particularly saturated and unsaturated hydrocarbons, especially light olefines.

BACKGROUND OF THE INVENTION

The mixtures carbon monoxide-hydrogen ($CO/H_2$) and carbondioxide-hydrogen ($CO_2$-$H_2$) are available from carbonaceous sources of non-petroleum origin, such as natural gas, by reforming with steam, and particularly coal by gasification. The production of hydrocarbons from synthesis gas, of which coal is the source, is expected to undergo considerable development.

This conversion has already been the subject of numerous research, but not giving entire satisfaction in the field of selectivity of the products formed.

A type of catalyst has been sought enabling the application of selective reactions with limitation of the growth of the chains of the products formed, and the use of carbon dioxide in place of carbon monoxide.

The use of carbon dioxide as carbon source has a fundamental interest, since $CO_2$ is available in abundance, for example, in hydrogen production units, whereas it is generally rejected entirely into the atmosphere. The production of hydrocarbons from $CO_2$ amounts consequently to economy of other carbon reserves whilst limiting rejects into the atmosphere as a source of pollution.

Catalysts based on copper and zinc are known at present as being the most effective systems in the synthesis of methanol. And recent investigations have shown that certain zeolite catalysts of the mordenite type are active in the conversion of methanol.

In French Pat. No. 2,320,923 catalysts have been proposed containing iron and copper on an ammonium Y type zeolite type support, for the synthesis of liquid hydrocarbons of the range of petrol and diesel fuel by the Fischer-Tropsch reaction.

In the same way, U.S. Pat. No. 4,180,516 and European Pat. No. 18,683 relate to the production of aromatic hydrocarbons from carbon monoxide and hydrogen in the presence of a heterogeneous catalyst, the first component being a chromium-zinc catalyst, the second being a zeolite of the ZSM type or a crystalline silicate of very specific composition, these catalysts being in admixture or separate.

On the other hand, according to French Pat. No. 2,019,913 the mordenite subjected to multiple alternate cycles of treatment with steam and of reflux in an inorganic acid is involved in a process for the conversion of hydrocarbons.

SUMMARY AND OBJECTS OF THE INVENTION

It now has been observed that the association of systems of metallic transition elements, such as copper, zinc and chromium with active mordenites enables the activity of the metallic catalysts to be increased and under certain conditions its selectivity to be modified. The magnitude of this effect of synergy in the conversion of the mixtures carbon monoxide/hydrogen and carbondioxide/hydrogen, as well as the nature of the products formed, alcohols, ethers or hydrocarbons, are a function of the type of mordenite.

The mordenites used are obtained from the sodium form of the mordenite with small pores of 4 to 5 Å, of which the formula of the elementary unit is $Na_7 Al_7 Si_{40} O_{94}$, $7H_2O$, the atomic ratio Si/Al being close to 6. They can be manufactured by the process described in French Pat. No. 1,411,753.

The various forms of mordenite applied according to the invention are the de-aluminised acid forms, obtained by two routes of de-aluminisation.

Chemical de-aluminisation consisting of successive treatments in a concentrated acid medium leads to the production of de-aluminised mordenite called type I.

Hydrothermic de-alumination, consisting of a series of alternate acid and hydrothermic treatments commencing with an acid treatment and ending with an acid treatment, leads from the sodium form of mordenite NaZ to the doubly de-aluminised mordenite called type II, and from the ammonium form $NH_4Z$ to the doubly de-aluminised mordenite called type III.

Mordenite crystallises in the orthorhombic system (group Cmcm) and the characteristics of some different types of mordenite engaged in the catalytic conversion of synthesis gases, CO-$H_2$ and $CO_2$-$H_2$ mixtures, are given below, according to the types: the positions in percentage weights, the atomic ratios Si/Al and $\Delta$P, the last on firing to 1000° C.

| TYPE | $SiO_2$ | $Al_2O_3$ | $Na_2O$ | $P_{1000°\ C.}$ | Si/Al Atomic |
|---|---|---|---|---|---|
| I | 88.1 | 3.3 | <0.1 | 8.6 | 22.6 |
| I | 92.8 | 1.2 | <0.1 | 6 | 65.6 |
| II | 97.1 | 1 | <0.1 | 1.9 | 82.4 |
| III | 98 | 0.7 | <0.1 | 1.3 | 120 |

The association active mordenite-metal transition elements is produced easily by methods calling upon either the intimate physical mixing of the active mordenite and the metallic contact mass, or the introduction into the mordenite of metallic transition elements by exchange or impregnation. This association can be envisaged in separate catalytic beds.

It has been observed that the mixed catalysts obtained by intimate physical mixing of a contact mass of copper and of zinc with an active mordenite show in the conversion of the mixtures carbon monoxide-hydrogen or carbon dioxide-hydrogen, an activity higher than that obtained with copper-zinc alone.

In the case of the mixture carbon oxide-hydrogen, the conversion into organic carbonaceous products under atmospheric pressure, at a temperature comprised between 200° and 350° C., and at a volumetric speed comprised between 2000 and 8000 $h^{-1}$, is approximately multiplied by 3 with the de-aluminised mordenite of type II.

The synergy effect with de-aluminised mordenite of type I is a function of the Si/Al ratio. Thus, the activity is multiplied by 10 with a Si/Al ratio of 66 and by 20 with a ratio Si/Al of 23.

The distribution of the products formed by catalytic conversion is also a function of the type of mordenite. Thus, with respect to the copper-zinc alone, there is noted with the de-aluminised mordenite of type II an increase in the formation of dimethyl ether at the expense of methanol, and the presence of saturated hydrocarbons. On the other hand, with the de-aluminised mordenites of type I, there is only obtained, from $CO/H_2$ mixtures, light hydrocarbons, containing from 2 to 4 carbon atoms in the molecule, of which the predominant product is ethane.

The association of the elements chromium and zinc with the de-aluminised active mordenites, by physical mixing of the active mordenites with a contact mass of the zinc chromite type or by deposition of these elements by impregnation, is of industrial interest.

It has been observed that the mixed catalysts obtained by physical mixing a zinc chromite with a mordenite show in the conversion of the mixtures $CO/H_2$ an activity higher than that obtained with zinc chromite alone. The synergy effect is in the vicinity of 2 with a de-aluminised mordenite of type I of ratio $Si/Al=27$. The products formed are hydrocarbons belonging essentially to the range $C_1-C_6$ as well as methanol and dimethyl ether. The distribution of the hydrocarbons is a function of the type of mordenite and particularly of the $Si/Al$ ratio. There is observed a maximum at $C_2$ with weakly de-aluminised mordenites ($Si/Al=10$), the latter changes to the $C_4$ when the degree of de-aluminisation increases. Thus, with mordenite of type III of ratio $Si/Al=120$, the $C_4$ hydrocarbons (principally isobutane) represent about 45% of CO converted into hydrocarbons.

Contrary to the copper-zinc-mordenite catalysts with which only saturated hydrocarbons are formed there, is obtained in this case a considerable proportion of olefines. The content of saturated substances increases with the growth of the chain. Beyond the cut $C_4$ there is observed only branched hydrocarbons; and isopentane being the sole product identified in the cut $C_5$.

The catalysts prepared by impregnation are obtained by deposition of metals from corresponding nitrate solutions. It has been observed that these catalysts have an activity per metal atom comparable with that of mixed catalysts, the products formed as well as their distribution being also similar.

These catalysts (mixed and impregnated) have been tested in a static reactor under pressure (30 to 100 bars) at a temperature of 250° to 350° C. as well as in the dynamic regime in a metallic reactor with a transverse fixed bed; under pressure up to 20 bars at a temperature comprised between 200° and 400° C. and a volumetric speed comprised between 1000 and 4000 $h^{-1}$. Appreciable differences in selectivity are observed between the autoclave reactor and the dynamic regime. This phenomenon is attributable to the very different contact times. Thus, with catalysts prepared by impregnation of mordenites of type III the maximum of $C_2$ in the dynamic regime passes to $C_4$ in the static regime, the production of $C_3$ remaining low in the two cases. This minimum of $C_3$ occurs also with mixed catalysts using mordenite of type III.

In the conversion of carbon dioxide-hydrogen mixtures, the manifestation of a synergistic effect has also been observed with mixed catalysts whilst being less than with carbon monoxide-hydrogen mixtures. The presence of mordenite is manifested by an increase in activity as a function of temperature beyond 200° C., whereas with the system Cu/Zn alone, the latter decreases regularly with temperature from 175° C. In this conversion the catalysts have been applied in a dynamic reactor with a fixed bed traversed at atmospheric pressure by the gaseous mixture to be converted.

The catalysts prepared by impregnation are obtained by deposition of metals from aqueous solutions of corresponding nitrates.

According to this modification it is possible to add the element chromium to the copper-zinc system.

It has been observed that the impregnated catalysts show also in the conversion of carbon monoxide-hydrogen mixtures an activity, per copper atom, comparable with that of mixed catalysts. The activity of the impregnated catalyst has been tested in a dynamic system at a temperature comprised between 200° and 400° C., at a volumetric speed comprised between 2000 and 8000 $h^{-1}$, and at atmospheric pressure with the same conditions as mixed catalysts.

According to a modification of the invention, the employment of the association copper-zinc transition elements and active mordenite in separate catalytic beds leads to a different result. This modification enables the observation that the nature of the products manufactured with a copper-zinc catalyst is modified by the addition of a mordenite bed, with a direction of passage of the gaseous mixture through the copper-zinc catalytic bed then the mordenite. In this precise case there is obtained essentially $C_2-C_3$ light olefines and dimethyl ether, propene being the predominant product. The observation of the conversion of an identical amount of carbon monoxide into organic products with respect to copper-zinc alone shows that the increase in activity of the mixed catalysts is due to a synergistic effect.

This modification of the application of the association copper-zinc catalyst and active mordenite opens a route to the direct conversion of synthesis gas into light olefines.

The application of the catalyst constituted by the association of at least two transition metal elements, such as copper-zinc and active mordenite in separate catalytic beds at different temperatures, the temperature of the second bed being higher than the first, the first bed being of metallic nature and the second of zeolitic nature, leads to the direct conversion of carbon dioxide-hydrogen mixtures into light olefines containing 2 to 4 carbon atoms with conversion ratios higher than those obtained with carbon monoxidehydrogen mixtures. The temperature difference between the two catalytic beds is at least of the order of 50° C.

The catalysts may be employed in separate reaction vessels.

The carbon dioxide-hydrogen mixture to be converted passes successively through the catalytic bed, the metallic bed being kept at a temperature of the order of 200°–250° C. and the zeolite bed being kept at temperatures of the order of 250° to 450° C.

The synthetic active mordenites are de-aluminised mordenites called types I, II and III.

The copper-zinc catalytic masses are industrial catalysts in which the copper and the zinc are introduced by co-precipitation preferably by mixing the soluble salt in the water of the catalytic metals and other metals, such as aluminium, namely in admixture or in simultaneous addition with an alkali carbonate, for example by the technique described in French Pat. No. 1,489,682 or that of R. G. Herman et al in J. Cat. 56, 407, 1979. The copper-zinc-aluminium catalysts may be activated by the in-situ formation of carbon dioxide in the course of the preparation of the catalyst at the moment when the metallic hydroxides and oxides are constituted. The copper-zinc contact masses of composition expressed in oxide, comprised between 40–70% CuO, 20–40% ZnO and 5 to 20% $Al_2O_3$, are particularly well suited to the practising of the conversion of carbon dioxide-hydrogen mixtures into light olefines. These masses are "activated" "in-situ" in a reaction vessel by reduction under hydrogen. Before and after the reaction the catalytic copper-zinc contact mass is studied under the same conditions as the conversion; ratio $H_2/CO_2$ identical and speed of passage of the gaseous mixture through the catalytic mass, in order to determine its capacity to convert methanol and thus verify that it has not been substantially modified in the course of time.

The spectrum of the products formed in the conversion of the mixtures $CO_2$-$H_2$ in separate catalytic beds at different temperatures under atmospheric pressure, in a dynamic system, at volumetric speed comprised between 2,500 and 5,000 $h^{-1}$, does not seem to depend direcly on the nature of the catalytic copper-zinc contact mass, but to be related with that of the active mordenite; certain of them can lead selectively to the formation of propene.

DETAILED DESCRIPTION OF PREFERRED EMBODIMENTS

Below are given examples which illustrate in non-limiting manner the preparation of the catalysts according to the invention, as well as their applications in the conversion of $CO/H_2$ and $CO_2/H_2$ mixtures. The figures for the results relating to each of the products formed correspond to their concentration in a mixture emerging from the reactor. The amounts of $CO_2$ formed in the conversion $CO/H_2$ are not shown, since they vary considerably not only from one type of catalyst to the next, but also in the course of the reaction with a tendency to diminution. Thus, with the catalysts Cu/Zn-mordenite type I at 250° C. the content of $CO_2$ in the mixture emerging from the reactor is 830 ppm at the start of the reaction; it is no more than 390 ppm after 23 hours under the same conditions. The formation of the carbon-dioxide is explained at least in part by the conversion reaction of the CO by the water formed in the course of the synthesis of the hydrocarbons but also present in mordenite. The gradual departure of the latter could explain the diminution of the $CO_2$ content with time.

EXAMPLE 1

Conversion of the mixture CO-$H_2$, in the presence of a mixed copper-zinc+mordenite catalyst in a single bed According to conventional methods, precipitation or mixing of salts followed by decomposition, the copper-zinc contact mass is prepared with the following composition by weight: CuO 63%; ZnO 27%; $Al_2O_3$ 10%.

The copper-zinc contact mass in the form of a powder of granulometry comprised between 50 and 500μ is intimately mixed physically with a powdered mordenite, of which the particle size is close to 40μ. The mordenite content in the catalyst is comprised between 20 and 80% and preferably 50%.

The various mordenites applied are type I mordenites obtained by de-aluminisation chemically of ratios Si/Al of 23 and 66; and the mordenite type II so-called doubly de-aluminised.

The final mixture (mordenite+copper-zinc) is then formed by the usual techniques, compression and extrusion. Then the catalyst is introduced into a fixed bed reactor where it is reduced in situ, at atmospheric pressure, by a current of hydrogen, at an hourly volumetric speed of 6,000 $h^{-1}$. The temperature is raised to 300° C. with a gradiant of 3° C. per minute and kept at the temperature plateau under these conditions for 6 hours.

After this activation treatment the hydrogen is replaced by a carbon-monoxide-hydrogen mixture, in which the ratio by volume $H_2/CO$ is 3. The hourly volumetric speed of the mixture CO-$H_2$ is 3,250 $h^{-1}$. In the course of the tests the temperature was varied from 225° to 350° C., and the conversion was carried out at atmospheric pressure.

The products formed were analysed by gas phase chromatography. The permanent gases CO and $CO_2$ were identified and quantified by detection by thermal conductivity and all of the organic products (hydrocarbons, alcohols and ether) by FID detection (flame ionisation detection).

Under these conversion conditions tests of catalytic activity for the conversion of the mixture $CO/H_2$ were carried out on the copper-zinc catalyst alone, then associated with various types of de-aluminised mordenites type I, II and III.

The results obtained are shown in table I, in which the products formed are represented by their chemical formula or abbreviations $nC_4$ denoting butane $-1$, and $iC_4$ isobutane, $C_5$ the $C_5$ hydrocarbons. The figures indicated show the concentration in the mixture emerging in ppm. $\Sigma C_3$ denotes the sum of $C_3H_6+C_3H_8$ and $\Sigma C$ the sum of the products formed as an equivalent of CO transformed $=(C_1)+(C_2)\times 2+\ldots+(C_n)\times n$. The following abbreviations denote respectively: MC the contact mass, t°C. the conversion temperature in degrees centigrade, tr (h) the reaction time in hours, M type I de-aluminised mordenite type I, M type II de-aluminised mordenite type II.

Examination of table I enables the following observations to be made: At 250° C. the copper-zinc catalyst alone produces essentially methanol and a little dimethyl ether. The increase in temperature up to 300° C. causes an increase of the dimethyl ether at the expense of the methanol, as well as increase in the methane. At 250° C. the carbon content in the mixture emerging in the form of organic substances corresponds to the conversion of 78 ppm of CO; this conversion changes little with increase of temperature up to 300° C.

TABLE I

| MC | t° C. | tr (h) | $CH_3OH$ | $(CH_3)_2O$ | $CH_4$ | $C_2H_4$ | $C_2H_6$ | $C_3H_6$ | $C_3H_8$ | $nC_4$ | $iC_4$ | $C_5^+$ | $\Sigma C$ |
|---|---|---|---|---|---|---|---|---|---|---|---|---|---|
| Cu/Zn | 250 | 47 | 63 | 6 | 3 | | | | | | | | 78 |
| | 275 | 48 | 46 | 12 | 8 | | 1 | | | | | | 78 |
| | 300 | 49 | 35 | 15 | 19 | | 2 | | | | | | 86 |
| Cu/Zn + | 250 | 3 | | | 2 | 12 | 278 | 43 | $(\Sigma C_3)$ | 3 | 33 | 6 | 885 |
| M type I | 275 | 4 | | | 3 | 17 | 355 | 69 | " | 7 | 48 | 7 | 1209 |
| Si/Al = | 300 | 5 h | | | 4 | 23 | 380 | 50 | 50 | 12 | 65 | 15 | 1493 |
| 23 | 325 | 5 h 40 | | | 7 | 30 | 413 | 30 | 99 | 14 | 58 | 16 | 1648 |
| | 350 | 6 h 30 | | | 18 | 35 | 448 | 46 | 84 | 12 | 37 | 13 | 1635 |
| Cu/Zn + | 225 | 1 | | | 2 | | 21 | 6 | 20 | 3 | 9 | 2 | 181 |
| M type I | 250 | 2 | | | 4 | 2 | 59 | 10 | 47 | 5 | 14 | 2 | 383 |
| Si/Al = | 275 | 2 h 30 | | | 7 | 5 | 117 | 14 | 69 | 11 | 16 | 3 | 623 |

TABLE I-continued

| MC | t° C. | tr (h) | CH$_3$OH | (CH$_3$)$_2$O | CH$_4$ | C$_2$H$_4$ | C$_2$H$_6$ | C$_3$H$_6$ | C$_3$H$_8$ | nC$_4$ | iC$_4$ | C$_5^+$ | Σ C |
|---|---|---|---|---|---|---|---|---|---|---|---|---|---|
| 66 | 300 | 3 | | | 8 | 8 | 176 | 16 | 72 | 11 | 12 | 3 | 747 |
| | 325 | 4 | | | 11 | 10 | 206 | 12 | 49 | 6 | 7 | 3 | 693 |
| Cu/Zn + | 250 | 3 | 9 | 38 | 1 | | | 3 | 3 | 3 | | | 119 |
| M type II | 275 | 6 | 21 | 53 | 3 | | 4 | | 9 | 4 | 5 | 2 | 211 |
| | 300 | 7 | 18 | 52 | 8 | | 13 | | 15 | 8 | 6 | 3 | 272 |
| | 325 | 27 | 11 | 35 | 22 | 1 | 31 | | 11 | 5 | 4 | 1 | 241 |

The application of type I mordenite produces the maximum effect of synergy. The activity is approximately multiplied by 5 at 250° C. and 10 at 300° C. There are formed only light hydrocarbons C$_2$-C$_4$, essentially saturated. The presence of small amounts of propene and ethylene is noted. Replacement of type I mordenite by that of type II attenuates the synergistic effect. In the products there are found both methanol and dimethyl ether obtained with copper-zinc and the light hydrocarbons obtained with type I mordenite.

EXAMPLE 2

Conversion of a CO$_2$-H$_2$ mixture, in the presence of a mixed copper-zinc+mordenite catalyst in a single bed The catalytic conversion of a carbon dioxide-hydrogen mixture was studied in the presence of the catalyst types applied in the preceding example, with an identical activation phase (H$_2$, VVH 6,000 h$^{-1}$ 300° C.).

In the treated carbon dioxide-hydrogen mixture the ratio H$_2$/CO$_2$ was 4, and the hourly volumetric speed of the CO$_2$/H$_2$ mixture under normal conditions of temperature and pressure 3,300 h$^{-1}$. In the course of the tests, the temperature was varied from 175° to 250° C. The gaseous effluents were analysed by gas phase chromatography according to the modalities defined in Example 1.

The results obtained are reported in table II.

TABLE II

| MC | t° C. | reaction time (h) | CH$_3$OH | (CH$_3$)$_2$O | CH$_4$ | ΣC | CO |
|---|---|---|---|---|---|---|---|
| Cu/Zn | 175 | 1 | 520 | | 2 | 522 | 1010 |
| | 200 | 3 | 460 | | 1 | 461 | 5000 |
| | 225 | 5 | 113 | | 1 | 114 | 15000 |
| | 250 | 6 | 30 | | 1 | 31 | 27000 |
| Cu/Zn + | 175 | 2 | 125 | 101 | 2 | 329 | 430 |
| M type I | 200 | 3 | 237 | 229 | 1 | 696 | 2300 |
| Si/Al = | 225 | 4 | 204 | 80 | 1 | 365 | 8000 |
| 66 | 250 | 5 | 70 | 4 | 1 | 79 | 19000 |
| Cu/Zn + | 175 | 2 | 526 | 23 | 2 | 574 | 550 |
| M type II | 200 | 3 | 636 | 59 | 2 | 756 | 3100 |
| | 225 | 5 | 218 | 18 | 3 | 257 | 10000 |
| | 250 | 6 | 78 | | 3 | 81 | 21000 |

The figures indicated represent concentration in ppm of the products formed in the outflowing mixture, the products formed are denoted by their formula and ΣC indicates the sum of the organic products formed, MC the contact mass, M type I the de-aluminised type I mordenite, M type II the de-aluminised type II mordenite.

On examining this table, it is observed that the conversion into methanol of the carbon dioxide-hydrogen mixture is greater, at low temperature, on the copper-zinc catalyst alone, than that of the carbon-monoxide-hydrogen mixture; and there is not on the contrary formation of dimethyl ether with CO/H$_2$.

It is observed that the catalysts: type I or type II mordenite associated with copper plus zinc, do not cause a synergistic effect at low temperature. And contrary to the results obtained with the carbon monoxide-hydrogen mixture no change in selectivity is observed, and this whatever the mordenite used. On the contrary, although the activity, for the synthesis of methanol from the mixture CO$_2$/H$_2$ falls very rapidly with the copper-zinc catalyst when the temperature increases above 175° C., it is observed with mordenite catalysts associated with copper-zinc that there is an increase beyond 200° C. This effect increases in the direction of the modifications of type I, type II mordenite. Thus at 200° C., with the copper-zinc+type II mordenite system, the activity is higher by 1.5 times that of copper-zinc.

EXAMPLE 3

Conversion of a carbon-monoxide-hydrogen mixture in the presence of chromium-zinc de-aluminised active mordenite catalysts The reaction is applied in a dynamic reactor under pressure requiring the prior shaping of the catalyst.

Granules of average diameter comprised between 0.6 and 1.6 mm are used, obtained by pelleting the powder, (pellets of 3 mm diameter) followed by granulation by crushing and sieving. In the case of the catalyst prepared by impregnation, before pelleting, a clay binder is incorporated in the proportion of 10% by weight to ensure suitable mechanical strength.

The reactor is constituted by a steel tube 1 cm in diameter; the CO$_2$/H$_2$ mixture is preheated to 150° C. The volume of catalyst employed is 10 cm3. A prior activation of the catalyst in situ is effected under H$_2$ atmospheric pressure at a temperature of 300° C. at a volumetric speed of 2000 h$^{-1}$ for 4 hours.

The pressure (H$_2$+CO) is varied from 10 to 20 bars, the volumetric speed from 1000 to 4000 h$^{-1}$ and the temperature from 200° to 400° C.

The results indicated below relate to contact masses associating a zinc chromite with a type I mordenite of ratio Si/Al=10 on the one hand (table III) and with a type III mordenite of ratio Si/Al=120 MGP 410 on the other hand (table IV) as well as a catalyst prepared by impregnation from a type II mordenite (table V). The zinc chromite content of the mixed catalysts was 25% by weight, the latter having been optimised by preliminary tests. The content of oxides expressed in $Cr_2O_3+ZnO$ of the impregnated catalyst was 10%; the atomic ratio Cr/Zn being 2.

As regards the results indicated in table IV there is noted at the beginning of the reaction a considerable variation in selectivity, with formation of $>C_6$ hydrocarbons whose content decreases rapidly as a function of time. After ten hours of reaction, the $C_1$ to $C_6$ hydrocarbons represent more than 80% of the CO converted.

The predominant products are ethylene 30% and isobutane 27%. A minimun in $C_3$ is observed very characteristic with these catalysts. The products beyond $C_3$ contain little olefines.

The influence of the type of mordenite on the selectivity is important. Thus with that of type I (Si/Al=10) associated with a zinc chromite, light $C_1$-$C_5$ hydrocarbons are obtained with a maximum of $C_2$; representing more than 90% of CO transformed, the complement comprising methanol, dimethylether and hydrocarbon traces. The content of olefines is considerable, and reaches under the conditions of the example 77% in the range $C_2$-$C_4$, the ethylene alone representing more than 40% of the CO transformed.

The catalysts prepared by impregnation from a dealuminised type III mordenite (table V) lead to results close to those obtained with the mixed catalysts (table IV). There is again found in the distribution of the products a maximum of $C_2$ (31.6%) and $C_4$ (25.6) and a minimum of $C_3$. However some appreciable differences are noted, in particular the increase of the methane (7 to 11%) and the decrease in the content of ethylene (11.8%) to the benefit of the ethane (19.8%).

TABLE III

| Dynamic reactor. MGP I + Si/Al = 10 75% by weight Volume of catalyst Granule of 0.6 to 1.6 mm Operating conditions: | Mixed catalysts zinc chromite 25% by weight 10 cm3 pressure 20 bars flow rate 20 Nl/h temperature 280° C. |
|---|---|
| Ratio by volume $CO/H_2$ = 1 | |

% of CO converted into

| $CH_4$ | $C_2H_4$ | $C_2H_6$ | $C_3H_6$ | $C_3H_8$ | $C_4H_{10}$ | $C_4H_8$ | $\Sigma C_5$ |
|---|---|---|---|---|---|---|---|
| 16.8 | 41.6 | 15,8 | 11.1 | 1.6 | 0.9 | 8.6 | 3.6 |

$\Sigma_1^5 C = 2.1$

TABLE IV

MGP III Si/Al = 120  75% by weight
Zinc chromite  25% by weight
Catalyst volume  10 cm3 by weight 6.6 g
Granules 0.6 to 1.6 mm
Operating conditions
Pressure 20 bars, flow rate 20 Nl/h.
Ratio by volume $CO/H_2$ = 1.
$\Sigma C = (C_1) + (C_2) \times 2 + (C_n)n$. $\Sigma C$ does not take into account small amounts of $CH_3OH$ and DME present ( ) % vol.

% CO converted into

| t° C. mean | $CH_4$ | $C_2H_4$ | $C_2H_6$ | $C_3H_6$ | $C_3H_8$ | $iC_4H_{10}$ | $nC_4H_{10}$ | $C_5$ | $C_6$ | $\Sigma_1^6 C$ |
|---|---|---|---|---|---|---|---|---|---|---|
| 245 | 7.6 | 29.6 | 3.2 | 0.2 | 3.7 | 26.8 | 1.2 | 18.2 | 9.5 | 0.5 |
| 285 | 7.2 | 16.3 | 11.8 | 0.1 | 5 | 27.2 | 1.4 | 19.7 | 11.3 | 1.6 |

TABLE V

Dynamic reactor. Impregnated catalyst.
MGP III Si/Al = 120
$(Cr_2O_3 + ZnO)$ = 10% by weight Cr/Zn = 2
Volume of catalyst 10 cm3 by weight 7.6 g

TABLE V-continued granules diameter 0.6 to 1 mm.
Operating conditions:
pressure 20 bars, flow rate 20 Nl/h. temperature 285° C.

% CO converted into

| $CH_4$ | $C_2H_4$ | $C_2H_6$ | $C_3H_6$ | $C_3H_8$ | $iC_4H_{10}$ | $nC_4H_{10}$ | $C_4H_8$ | $C_5$ | $C_6$ |
|---|---|---|---|---|---|---|---|---|---|
| 11.5 | 11.8 | 19.8 | 3.4 | 5.8 | 22.6 | 1.2 | 1.8 | 14.5 | 7.6 |

$\Sigma_1^6 C = 0.38$.

EXAMPLE 4

Conversion of carbon-monoxide-hydrogen on copper-zinc-chromium impregnated catalysts Type I or II mordenite in powder form is subjected to dynamic processing under vacuum, at a temperature of 500° C., for 2 hours. After cooling to room temperature, the mordenite is impregnated with a supernatant aqueous solution containing a mixture of copper, zinc and chromium nitrate, prepared from crystallised salts $Cu(NO_3)_2, 3H_2O$, $Zn(NO_3)6H_2O$, and $Cr(NO_3)_39H_2O$; the metals, copper, zinc, chromium being respectively in the atomic ratios 2Cu/1Zn/0.3Cr. After two hours impregnation, the water is evaporated by treatment under dynamic vacuum at 60° C. The catalyst is then subjected to complementary drying in the oven at 100° C. The contents by weight in percentages, expressed in oxides of the different catalysts prepared and applied are CuO: 4.9, ZnO: 2.5 $Cr_2O_3$: 0.7. Also in type I mordenite, the ratio Si/Al was 23.

These catalysts were tested in a dynamic reactor at atmospheric pressure under identical operating conditions with those of Example 1. The $CO-H_2$ mixture subjected to the conversion was in the ratio $H_2/CO=3$, the hourly volumetric speed was 3,250 h$^{-1}$. The results of these conversions of the two types of metallically impregnated catalysts are given in table VI. Tests were carried out at temperatures of 250° to 400° C., the concentrations of the products formed are indicated in ppm in the mixture flowing out, $\Sigma C$ denoting the total concentration of the organic substances formed.

TABLE VI

| Type of mordenite | t°C. | $CH_3OH$ | $(CH_3)_2O$ | $CH_4$ | $C_2H_4$ | $C_2H_6$ | $C_3$ | $\Sigma C$ |
|---|---|---|---|---|---|---|---|---|
| II | 250 | 2 | | | | | | 2 |
| | 350 | 3 | | | 1 | | | 5 |
| | 400 | 9 | 3 | 7 | | 1 | | 32 |
| I Si/Al ~23 | 250 | 4 | | 3 | | | | 10 |
| | 350 | 6 | 3 | 23 | | | | 58 |
| | 375 | 14 | 5 | 41 | | | | 106 |
| | 400 | 25 | 3 | 38 | | | | 107 |

EXAMPLE 5

Conversion of a carbon monoxide-hydrogen mixture in the presence of two separate beds of catalyst The tests were carried out in a laboratory reactor, under a dynamic flow, equipped so as to accept two separate beds of catalyst. The first bed was charged with copper-zinc catalyst alone, effecting the reduction of this catalyst under the conditions described in Example 1. Then, the $CO/H_2$ mixture in which the ratio $H_2/CO$ was 3, was passed at atmospheric pressure at an hourly volumetric speed of 6,600 $h^{-1}$, expressed under normal conditions of temperature and pressure, the temperature being 250° C. The results obtained are shown in table VII.

The experiment was repeated under the same conditions as previously by placing in the second bed of the reactor the de-aluminised type I mordenite, in which the ratio Si/Al was 66, the volumes of the two catalysts being identical. Tests were carried with a $CO/H_2$ mixture of ratio $H_2/CO$ of 3, at 250° C., under atmospheric pressure, namely a VVH of 3,300 $h^{-1}$. The results are reported in table VII in which are shown the concentrations of the mixtures flowing out expressed in ppm of products formed; $\Sigma C$ denoting the sum of the organic substances obtained.

TABLE VII

| Catalyst | $CH_3OH$ | $(CH_3)_2O$ | $CH_4$ | $C_2H_4$ | $C_2H_6$ | $C_3H_6$ | $C_3H_8$ | $C_4^+$ | $\Sigma C$ |
|---|---|---|---|---|---|---|---|---|---|
| Cu/Zn 1 bed | 78 | 3 | 5 | | | | | | 89 |
| Cu/Zn M type I Si/Al 66 2 beds | | 14 | 2 | 3 | | 15 | 1 | 2 | 92 |

EXAMPLE 6

Conversion of a carbon dioxide-hydrogen mixture in the presence of two separate beds of different catalysts at the same temperature The tests were carried out in a single cell type reactor with separate beds. The first bed was charged with 200 mg of copper-zinc catalyst activated by the in situ formation of carbon dioxide in the course of the preparation, of composition $60CuO-30ZnO-10Al_2O_3$ called 71 A. In the second bed of the reactor was placed 200 mg of de-aluminised type I synthetic mordenite derived from the chemical de-aluminisation of mordenite by successive treatments in a concentrated acid medium of ratio Si/Al 70.

The catalytic copper-zinc mass was "activated" "in situ" by reduction under hydrogen (6,250 $h^{-1}$) at 300° C. for 6 hours, after a rise in temperature at 3° C. per minute.

The tests were carried out with a $CO_2/H_2$ mixture of ratio $H_2/CO_2$ of 4, at an atmospheric pressure at a speed of 3,300 $h^{-1}$. Three tests were carried out respectively at 200°, 225° and 250° C.

The results are collected in table VIII in which are shown the concentrations of the mixtures flowing out expressed in ppm of substances formed, $\Sigma C$ denoting the sum of the organic substances obtained.

TABLE VIII

| Catalyst | $\theta$ °C. | products | | | $\Sigma C$ |
|---|---|---|---|---|---|
| | | $CH_4$ | MeOH | $Me_2O$ | |
| Cu/Zn | 200 | 1 | 154 | 150 | 455 |
|  | 225 | 1 | 324 | 115 | 555 |
| M type I Si/Al 70 | 250 | 1 | 220 | 19 | 259 |

From reading this table, there is seen only the formation of methanol and of dimethylether.

EXAMPLE 7

Conversion of two types of carbon monoxide-hydrogen and carbon dioxide-hydrogen mixtures in the presence of two separate beds of catalysts of different nature at different temperatures The tests were carried out in two cells into which were passed successively the gaseous mixtures which were kept at different temperatures.

The first cell was charged with 200 mg of copper-zinc catalyst activated in the course of preparation by $CO_2$ of the same composition $60CuO-30ZnO-10Al_2O_3$ as previously. In the second reaction cell was placed 200 mg of synthetic mordenite of which the atomic ratio Si/Al was 15, called de-aluminised type I mordenite derived from the chemical de-aluminisation of synthetic mordenite by successive treatments in a concentrated acid medium.

The copper-zinc catalytic mass was "activated" in place in the reaction cell by effecting the reduction of these catalysts under the conditions described in Example 6.

Then, the mixture $CO/H_2$, in which the ratio $H_2/CO$ was 3, was passed, at atmospheric pressure at a speed of 3,300 $h^{-1}$. In the first cell the reaction took place at a temperature of 250° C., in the second, four tests were carried out at increasing temperatures from 250° to 400° C. The results obtained are shown in table II.

The experiment was repeated under the same conditions as previously by converting a $CO_2/H_2$ mixture in which the ratio $H_2/CO_2$ was 4, at atmospheric pressure, by passing said mixture successively through the two cells at a volumetric speed of 3,300 $h^{-1}$.

In the first cell, the temperature was 200° C., in the second cell a series of 4 tests were carried out at increasing temperatures respectively of 250°, 300°, 350° and 400° C.

The comparative results are collected in table IX in which are shown the concentrations of the mixtures flowing out, expressed in ppm of substances formed. $\Sigma C$ denoting the sum of the organic substances obtained. The catalysts are denoted by Cu/Zn and MGP 202 for the mordenite.

TABLE IX

| Gaz | $\theta_{Cu/Zn}$ °C. | $\theta_{MGP}$ 202 °C. | Products (ppm) | | | | | | | | | |
|---|---|---|---|---|---|---|---|---|---|---|---|---|
| | | | MeOH | Me$_2$O | CH$_4$ | C$_2$H$_4$ | C$_2$H$_6$ | C$_3$H$_6$ | C$_3$H$_8$ | nC$_4$ | iC$_4$ | C$_5^+$ | ΣC |
| CO/H$_2$ | 250 | 250 | | | 2 | 5.5 | + | 4.5 | + | | 1.8 | | 34 |
| | | 300 | | | 2 | 6 | + | 4 | + | | 1.5 | | 32 |
| | | 350 | | | 4 | 8 | + | 3 | + | + | 0.5 | | 31 |
| | | 400 | | | 4 | 13 | + | 3.5 | + | + | + | | 43.5 |
| CO$_2$/H$_2$ | 200 | 250 | 37 | 29 | 3 | 4 | + | 9 | 11 | 2 | 25 | 3 | 289 |
| | | 300 | | | 3 | 35 | 2 | 12 | 17 | 4 | 18 | 2.5 | 261 |
| | | 350 | | | 6 | 51.5 | 3 | 18 | 22 | 3 | 8 | 0.5 | 289 |
| | | 400 | | | 16 | 73.5 | 5 | 16 | 22 | 3 | 4.5 | 0.5 | 322 |

From reading table IX, it is noted that the conversions obtained with the mixture CO$_2$-H$_2$ were greater than those obtained with CO-H$_2$.

EXAMPLE 8

Conversion of a carbon dioxide-hydrogen mixture in the presence of two separate beds of catalyst of different nature at different temperatures, for studying the influence of the nature of the copper-zinc catalyst and that of zeolite on the distribution of the products formed.

The tests were carried out in two separate cells. In the mixture subjected to the conversion CO$_2$-H$_2$ and CO$_2$ were in a ratio 4. The gas passed through the cells containing the catalysts at a volumetric speed of 3,300 h$^{-1}$, at atmospheric pressure.

Three series of tests were made, in the course of which the reaction temperature in the first cell was 200° C., and in the second cell the temperature was raised at each test, the first test being carried out at 250° C. and the fifth at 450° C.

In the first series of tests the cell 1 was charged with 200 mg of a copper-zinc catalytic mass 60CuO-30ZnO-10Al$_2$O$_3$ of type 71 A. In the two other series of tests the cell was charged by a catalyst of so-called S1 type, of similar composition, but of different nature, prepared according to French Pat. No. 1,489,682 by co-precipitation, mixing the soluble salt in the liquor of the catalytic metals the pH in the course of the co-precipitation being kept at less than 0.5 units from neutrality.

In the two first series of tests, cell 2 was charged with 200 mg of type I de-aluminised mordenite derived from the chemical de-aluminisation of synthetic mordenite by successive treatments in a concentrated acid medium, of which the atomic ratio Si/AL was 15, MGP 202. In the third series of tests the cell was charged with 200 mg of type II de-aluminised synthetic mordenite obtained by hydrothermic de-aluminisation consisting of a series of alternate acid and hydrothermic treatments from ammonium formed mordenite and of atomic ratio Si/Al 120, called MGP 410.

The copper-zinc catalytic masses were "activated" in place in the reation cell by carrying out reduction of the catalysts under the conditions described in Example 6. Then, the gaseous mixture CO$_2$/H$_2$ was made to pass into the two reaction vessels under the conditions of speed, temperature and pressure indicated previously.

The results obtained in the three series of tests are collected in the table below.

TABLE X

| Catalyst | $\theta_{MGP}$ °C. | Products | | | | | | | | | | |
|---|---|---|---|---|---|---|---|---|---|---|---|---|
| | | MeOH | Me$_2$O | CH$_4$ | C$_2$H$_4$ | C$_2$H$_6$ | C$_3$H$_6$ | C$_3$H$_8$ | nC$_4$ | iC$_4$ | C$_5^+$ | ΣC |
| 71 A 202 | 250 | 37 | 29 | 3 | 4 | + | 9 | 11 | 2 | 25 | 3 | 289 |
| | 300 | | | 3 | 35 | 2 | 12 | 17 | 4 | 18 | 2.5 | 261 |
| | 350 | | | 6 | 51.5 | 3 | 18 | 22 | 3 | 8 | 0.5 | 289 |
| | 400 | | | 16 | 73.5 | 5 | 16 | 22 | 3 | 4.5 | 0.5 | 325 |
| | 450 | | | 30 | 90 | 7 | 14 | 20 | 1.5 | 2 | + | 340 |
| S1 202 | 250 | 19 | 20 | 2 | 14 | 10 | 12 | 13 | 4 | 50 | 6 | 430 |
| | 300 | | | 4 | 48 | 11 | 24 | 26.5 | 8 | 29 | 4.5 | 444 |
| | 350 | | | 9 | 78 | 13 | 34 | 38 | 6.5 | 16 | 2 | 502 |
| | 400 | | | 32 | 96 | 11.5 | 19 | 35 | 4 | 8 | 0.5 | 490 |
| | 450 | | | 76 | 102 | 11 | 19 | 26 | 2.5 | 3 | | 465 |
| S1 410 | 250 | 110 | | 1 | 3 | | 36 | | 8 | 25 | 10 | 381 |
| | 300 | 54 | | 1.5 | 8 | + | 64 | 1 | 13.5 | 19 | 9.5 | 381 |
| | 350 | 20 | | 3 | 13 | + | 85 | 2 | 13 | 12 | 4 | 426 |
| | 400 | 15 | | 5 | 14.5 | + | 86 | 2 | 12 | 6 | 3.5 | 403 |
| | 450 | 15 | | 12 | 30 | + | 90 | 2 | 13 | 5 | 2.5 | 447 |

The spectrum of the products formed does not seem to depend on the nature of the copper-zinc catalytic mass but to be connected with that of the zeolite; certain of them can lead selectively to propene.

We claim:

1. A catalyst for the conversion of synthesis gas into organic compounds, in particular saturated and unsaturated hydrocarbons, consisting essentially of:

a first component comprising a mixture of the reduced form of least two transition metals selected from the group consisting of copper, zinc and chromium, one of said selected transition metals being zinc;

a second component comprising an active mordenite selected from the group consisting of mordenites derived from the chemical de-aluminization of mordenite by successive treatments in a concentrated acid medium and doubly de-aluminized mordenites derived from hydrothermic de-aluminization consisting of a series of alternate acid and hydrothermic treatments, beginning and terminating in an acid treatment, from the sodium form, NaZ, or ammonium form, NH$_4$Z, of mordenite, said first and second components being in intimate admixture.

2. The catalyst of claim 1 wherein said intimate admixture has been obtained by the intimate physical mixing of a metallic contact mass comprising an oxidized form of said selected transition metals with said active mordenite followed by the reduction of the oxidized form of said selected transition metals in a hydrogen current.

3. The catalyst of claim 1 wherein said intimate admixture has been obtained by impregnating said active mordenite with an aqueous solution of zinc nitrate, said solution further comprising a solute selected from the group consisting of copper nitrate, chromium nitrate and mixtures thereof, followed by the reduction of said nitrates to the reduced form of the selected transition metals.

4. A catalyst according to claim 1, wherein said first component comprises chromium-zinc and said second component comprises said de-aluminized mordenite derived from chemical de-aluminization of mordenite by said successive treatment in a concentrated acid medium for the production of $C_2$ hydrocarbons.

5. A catalyst according to claim 1, wherein said first component comprises copper and zinc and said second component comprises said doubly de-aluminized mordenite for the production of $C_4$ hydrocarbons.

6. A catalyst according to claim 1, wherein the active mordenite has been derived from the chemical de-aluminization of mordenite by said successive treatments in concentrated acid medium, said catalyst comprising means to convert a carbon monoxide-hydrogen mixture to ethylene.

7. A catalyst according to claim 1, wherein said first component comprises copper and zinc and said second component comprises said de-aluminized mordenite derived from the chemical de-aluminization of mordenite by said successive treatment in a concentrated acid medium, the ratio of Si/Al being about 60, said catalyst constituting means to produce $C_2$-$C_3$ hydrocarbons from a carbon monoxide-hydrogen mixture.

* * * * *